(12) United States Patent
Pruckner et al.

(10) Patent No.: US 8,936,470 B2
(45) Date of Patent: Jan. 20, 2015

(54) DEVICE FOR QUICKLY STOPPING A MEDICAL, IN PARTICULAR DENTAL, DRILLING TOOL

(75) Inventors: Christian Pruckner, Vienna (AT); Thomas Jindra, Bürmoos (AT); Georg Watzek, Vienna (AT); Ewald Unger, Vienna (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 32 days.

(21) Appl. No.: 13/818,297

(22) PCT Filed: Aug. 23, 2011

(86) PCT No.: PCT/EP2011/064442
§ 371 (c)(1),
(2), (4) Date: Feb. 21, 2013

(87) PCT Pub. No.: WO2012/025515
PCT Pub. Date: Mar. 1, 2012

(65) Prior Publication Data
US 2013/0149660 A1   Jun. 13, 2013

(30) Foreign Application Priority Data

Aug. 24, 2010   (EP) .................................... 10173768

(51) Int. Cl.
*A61C 3/02*      (2006.01)
*A61B 17/16*     (2006.01)
(Continued)

(52) U.S. Cl.
CPC . *A61C 3/02* (2013.01); *A61B 17/16* (2013.01); *A61B 17/1626* (2013.01);
(Continued)

(58) Field of Classification Search
USPC ..................... 433/27, 28, 103, 105, 106, 114, 433/125–129, 165, 166, 175; 606/80, 172, 606/173; 408/8–10, 12, 5, 6, 11, 14; 388/930, 932, 937; 128/898; 340/680, 340/686.1; 384/92; 451/9–11; 76/108.1–108.6; 175/50
See application file for complete search history.

(56) References Cited

U.S. PATENT DOCUMENTS 6,665,948 B1 *  12/2003  Kozin et al. ..................... 33/833
2002/0025504 A1 *  2/2002  Satake et al. ................... 433/106
(Continued)

FOREIGN PATENT DOCUMENTS

EP            1269933       1/2003
WO        WO2009/138242    11/2009

OTHER PUBLICATIONS

International Search Report for PCT/EP2011/064442 mailed Dec. 29, 2011.

*Primary Examiner* — Ralph Lewis
(74) *Attorney, Agent, or Firm* — Klarquist Sparkman, LLP

(57) ABSTRACT

A device for quickly stopping a medical or dental drilling tool includes a drilling tool having a body extending between a connection end and a working end and having a longitudinal extension along a longitudinal axis of the drilling tool. The drilling tool has a hollow outer shell in which a probe is held that can be moved along the longitudinal axis so that a part of the probe can be moved out of the shell through an opening. The probe is designed as an elongated pin, and its first end facing the connection end is held in the interior of the shell. An electromagnetic sensor for detecting relative movement between the shell and the probe is arranged along the longitudinal extension of the body. The drilling tool has a channel for a treatment fluid extending along the longitudinal axis.

20 Claims, 5 Drawing Sheets

(51) Int. Cl.
*A61C 1/00* (2006.01)
*A61C 1/06* (2006.01)
*A61C 19/06* (2006.01)
*A61C 8/00* (2006.01)
*A61C 1/05* (2006.01)
*A61B 19/00* (2006.01)

(52) U.S. Cl.
CPC .............. *A61C 1/003* (2013.01); *A61C 1/0069* (2013.01); *A61C 1/06* (2013.01); *A61C 19/063* (2013.01); *A61C 8/0089* (2013.01); *A61C 1/055* (2013.01); *A61B 17/1644* (2013.01); *A61B 17/1673* (2013.01); *A61B 2019/305* (2013.01)
USPC .............. 433/215; 433/27; 433/106; 433/125; 318/6

(56) References Cited

U.S. PATENT DOCUMENTS

2008/0243123 A1* 10/2008 Gordils Wallis et al. ....... 606/80
2009/0245956 A1 10/2009 Apkarian et al.

* cited by examiner

DEVICE FOR QUICKLY STOPPING A MEDICAL, IN PARTICULAR DENTAL, DRILLING TOOL

CROSS REFERENCE TO RELATED APPLICATION

This is the U.S. National Stage of International Application No. PCT/EP2011/064442, filed Aug. 23, 2011, which was published in German under PCT Article 21(2), which in turn claims the benefit of European Patent Application No. 10173768.2, filed Aug. 24, 2010, both of which are incorporated herein by reference.

BACKGROUND

1. Field

This application concerns a device for quickly stopping a medical or dental drilling tool, also referred to as a "quick stop" device.

2. Description of Prior Art

Such a class of device is disclosed, for example, in the patent application DE 10 2008 032 704 A1. The device comprises a drilling tool with two concentric parts which are axially slidable against each other, wherein the inner part is pre-stressed against the outer part axially in the drilling direction by means of a spring and, if there is no counteracting force or such is insufficient, slightly projects with its tip over the tip of the outer part in the drilling direction. Furthermore, a device is provided that interrupts the drive of the drilling tool when the inner part is shifted axially in relation to the outer part, wherein the device is connected to an electromagnetic sensor that detects the axial sliding of the inner part against the outer part.

The sensor is designed as an end position sensor that is located on the rear end of the drilling tool (the end connected to a drive) and detects any movement of the broadened end of the inner part, which protrudes from the outer part of the drilling tool. However, this structure is of considerable disadvantage when the quick stop device is supposed to be integrated into a handpiece head, particularly a contra-angle handpiece head, since, particularly due to the constricted space in the handpiece head there is hardly any room for the sensor and for the displacement of the broadened end of the inner part. Moreover, the end position sensor hinders the drilling tool from being connected to a fluid supply.

SUMMARY

Described below are embodiments of a device for quickly stopping a medical or dental drilling tool which does not have the disadvantages mentioned above and which is in particular designed in such a way that it accommodates the cramped conditions in a handpiece head, particularly in a contra-angle handpiece head.

According to an embodiment this task is resolved by a device for the quick stop of a medical or, particularly dental, drilling tool that comprises: a drilling tool with a connection end for connecting to a drive, an abrasive working end for removing material, and a body extending between the connection end and the working end having a longitudinal extension extending along a longitudinal axis of the drilling tool, wherein the drilling tool has a hollow outer shell, in which a probe pre-tensioned by a spring element is held, that can be moved along the longitudinal axis relative to the outer shell, so that at least a part of the probe is moveable out of the outer shell through an opening in the outer shell at the working end, wherein the probe is designed as an elongate pin extending along the longitudinal axis with a first end facing the connection end and a second end facing the working end, and an electromagnetic sensor for the detection of relative motion between the outer shell and the probe, wherein the first end of the probe facing the connection end is held in the interior of the hollow outer shell of the drilling tool, the electromagnetic sensor is located along or within the longitudinal extension of the body of the drilling tool, and the drilling tool has a channel for a treatment fluid extending along its longitudinal axis.

Through the arrangement of the electromagnetic sensor along or within the longitudinal extension of the body of the drilling tool and the first end of the probe facing the connection end in the interior of the hollow outer shell of the drilling tool, no additional space for the sensor is required in the handpiece at the rear end (the connection end) of the drilling tool. This furthermore makes it possible to connect the drilling tool at its connection end to a fluid source for a treatment fluid and/or cooling fluid and to guide the treatment fluid through the drilling tool along a guiding channel extending along the longitudinal axis.

The electromagnetic sensor within the meaning of this application includes both sensors that react substantially or exclusively to electrical fields, for example capacitative sensors, and sensors that substantially or exclusively react to magnetic fields, for example inductive sensors or magnetic sensors.

In accordance with one embodiment, the electromagnetic sensor comprises an inductive sensor with at least one coil and one coil core, for example a hard- or soft-magnetic magnetic element, particular a ferrite body, wherein said at least one coil and coil core can be moved relative to one another, in particular due to the relative movement of the probe to the outer shell. Preferably, the coil core with the probe can be moved along the longitudinal axis of the drilling tool and relative to said at least one coil. The term "inductive sensor" can, in accordance with the invention, mean either a sensor that, due to the previously mentioned relative movement, detects a change in inductance in the coil (wherein this sensor has a magnetically soft element) or a sensor that, due to the previously mentioned relative movement, detects an induction voltage generated in the coil (wherein this sensor has a permanent magnetic element).

In accordance with one embodiment, the electromagnetic sensor comprises a magnetic sensor, particularly a Hall effect sensor or a reed sensor, and at least one magnetic element, wherein the magnetic sensor and said at least one magnetic element can be moved relative to one another due to the relative movement of the probe with respect to the outer shell.

In accordance with one embodiment, the electromagnetic sensor comprises a capacitative sensor with at least two metallic electrodes, forming a capacitor, wherein—due to the relative movement of the probe with respect to the outer shell—an electrode can be moved relative to another electrode. The capacitative sensor preferably comprises at least two substantially plate-shaped electrodes, as well as a measurement electrode that can be moved with the probe along the longitudinal axis of the drilling tool and relative to the two substantially plate-shaped electrodes.

The embodiments mentioned above, particularly the sensors used, have several advantages: The sensors are designed as contact-free sensors, and work largely without wear. The dimensions of the sensors are small, so that at least parts of the sensors can be integrated into the drilling tool and/or can be attached to or in the vicinity of the drilling tool, without hindering or influencing the use of the drilling tool. The sensors or at least parts thereof are resistant to external influences, such as treatment fluids, liquids, vapors, cleaning agents and particles, or at least parts of the sensors can be integrated into an enclosure in order to make them resistant to external influences. In particular, at least parts of the sensors, for example a magnetic element, a ferrite body or a plate/electrode of the capacitor, can be minimized in such a way that they can be located in the hollow outer shell or in the interior of the hollow outer shell of the drilling tool, particularly preferably connected to the probe, and despite their being minimized, surprisingly generate a sufficiently strong sensor-signal, capable of analysis or processing. The diameter or width of a sensor element connected to the probe, for example a magnetic element, a ferrite body, or a plate/electrode of the capacitor, is preferably less than 3.0 mm, particularly preferably less than 2.5 mm.

In accordance with one embodiment, the channel for a treatment fluid comprises a borehole in the outer shell of the drilling tool and/or penetrates the spring element pre-tensioning the probe. In accordance with another embodiment, the channel for a treatment fluid comprises a borehole in the probe of the drilling tool. The probe preferably has a guide section, whose diameter corresponds roughly to the inner width of the hollow outer shell in which it is held, so that the guide section is supported on the inner wall of the hollow outer shell, and a second section that is separated from the inner wall of the hollow outer shell by a gap, particularly an annular gap, wherein the gap forms at least a part of the channel for a treatment fluid. Particularly preferably, the borehole in the probe that forms the channel for a treatment fluid and the gap are connected with one another by a cross hole in the probe.

These embodiments have the advantage that, despite at least a part of the sensor being integrated into the drilling tool, it is possible to implement the treatment fluid being channeled through the interior of the drilling tool and dispensed directly at the tip or at the abrasive working end of the drilling tool, thus bringing about particularly effective cooling of the drilling tool and the treatment site directly where the abrasive working end of the drilling tool meets the bone.

In accordance with one embodiment, at its second end, facing the working end, the probe comprises a probe tip that is arranged eccentrically to the longitudinal axis. This is particularly advantageous when the drilling tool is placed at a slant to the material to be drilled or the thickness of the material to be bored varies, since, through the rotating, eccentrically arranged probe tip, a larger surface of the drilled material is sampled, and thus the thinnest area of the material can be better detected. The probe tip may, furthermore, be equipped with a cutting surface or an abrasive surface to remove tissue.

The probe tip placed eccentrically to the longitudinal axis also permits the probe tip to be rotated by the hollow outer shell of the drilling tool, wherein preferably the eccentric probe tip comprises a driven surface facing the longitudinal axis that contacts a drive surface, particularly a substantially centric drive surface, on the hollow outer shell, so that the drive motion of the hollow outer shell can be transmitted to the probe and the probe rotates together with the hollow outer shell.

In accordance with one embodiment, a medical, particularly dental, treatment device comprises a device for the quick stop of a medical, particularly dental, drilling tool, a drive for the drilling tool, a handpiece to connect to the drilling tool, and a control and/or regulatory device to receive a sensor signal generated by the electromagnetic sensor and to stop the drive, wherein at least a part of the electromagnetic sensor is arranged on the handpiece, wherein in particular a part of the electromagnetic sensor is attached, or can be attached, directly to the handpiece, and is thus not attached directly to the drilling tool. In other words, the sensor thus consists of two parts, one of which is connected in a fixed or detachable manner directly to the handpiece and a second of which is connected directly to the drilling tool, so that when the handpiece and the drilling tool are separated from one another, one part of the sensor remains on the handpiece and one part of the sensor on the drilling tool.

In accordance with one embodiment, the sensor is provided for in the area of the tool insertion opening of the handpiece. This is particularly advantageous when the drilling tool has a section with a larger diameter (in comparison with the diameter of another section of the drilling tool), for example when that section has a larger diameter in or on which at least one part of the sensor is provided for. The tool insertion opening can, in particular, have a section with an enlarged diameter, on which the part of the sensor directly connected to the handpiece is provided for and into which the section of the drilling tool with the greater diameter can be incorporated. In this manner, the sensor is located on the handpiece, without other components of the handpiece or their arrangement within the handpiece having to be influenced or changed, or other components of the handpiece influencing the sensor or the functioning or operation of the sensor.

In accordance with a preferred embodiment, a first part of the sensor is provided for on the drilling tool and can be detachably connected to the handpiece by connecting the drilling tool to the handpiece, and a second part of the sensor can be attached directly to the handpiece via a detachable connection mechanism, particularly on the outer shell of the handpiece, so that, when the first and second parts of the sensor are attached to the handpiece, the first and second parts of the sensor operatively interact with one another. The sensor is thus advantageously entirely detachable from the handpiece, and can, for example, be connected to various different handpieces or cleaned or serviced separately from the handpiece. Particularly preferably, the first part of the sensor and/or the second part of the sensor can be located on the outer side of the outer shell and/or outside the outer shell of the handpiece. This permits any handpiece to be connected to the sensor or the quick stop device and the drill to be quickly stopped with any handpiece, without the handpiece needing to be adapted.

Following is a description of embodiments with reference to the accompanying drawings:

DETAILED DESCRIPTION

Figure 1:
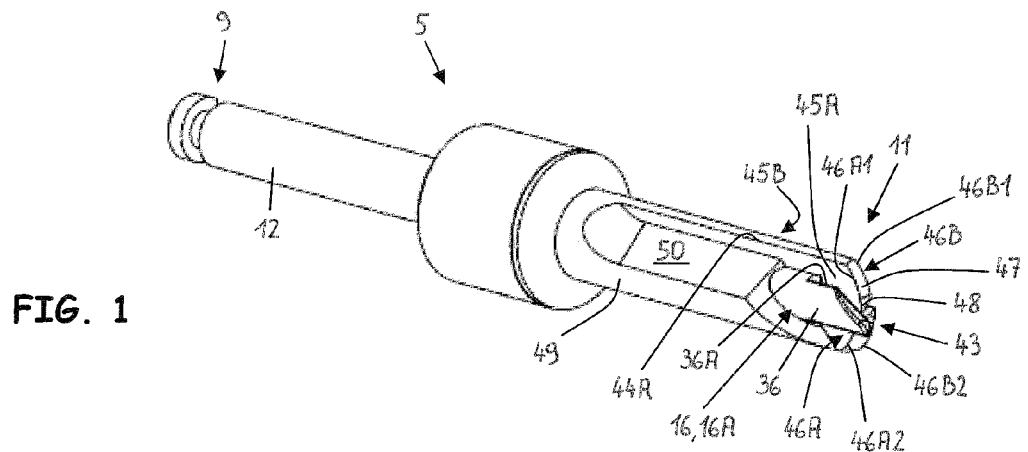
FIG. 1 shows a perspective view of an embodiment of a medical or dental drilling tool quick stop device.
Figure 2A:
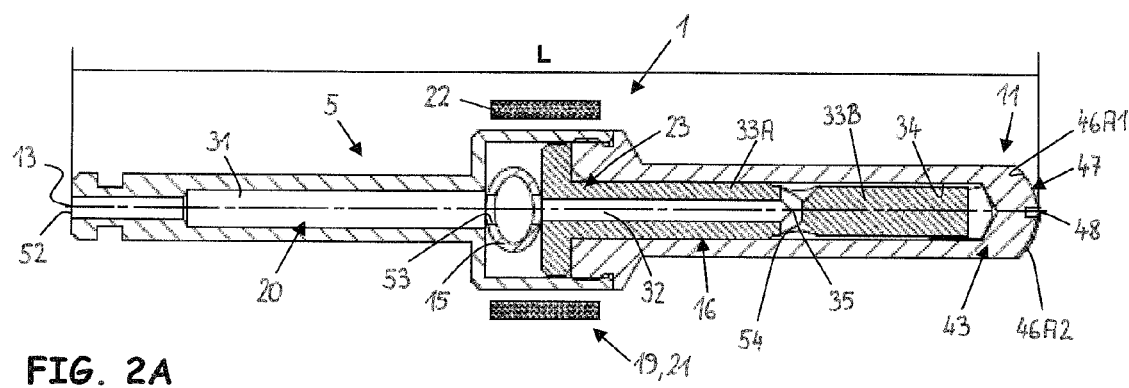
FIG. 2A shows a cross-section through an embodiment of a device for the quick stop of a medical, particularly dental, drilling tool having an inductive sensor, illustrating a first sectional plane.
Figure 2B:
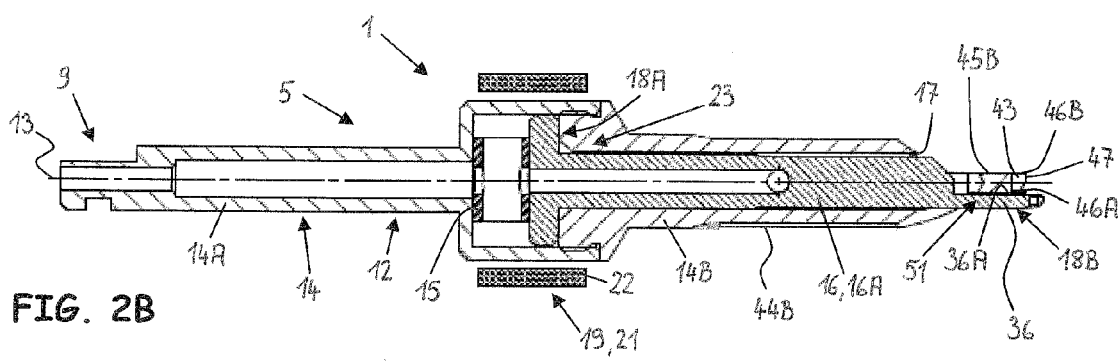
FIG. 2B shows a cross-section through the device shown in FIG. 2A illustrating a second sectional plane that is rotated through an angle of 90 degrees relative to the first sectional plane.

FIGS. 1, 2A, and 2B show a drill or drilling tool 5 that can be used for a device 1 for the quick stop of a medical, particularly dental, drilling tool 5. The drilling tool 5 has an elongated body 12 with a longitudinal extension L extending along a longitudinal axis or central axis or rotational axis 13. The ends of the body 12 are designed as a connection end 9 for connecting to a drive 10 (see FIG. 6) and as an abrasive working end 11 for removing material. The body 12 furthermore comprises a hollow outer shell 14 (see FIG. 2B) and a probe 16 held therein, which can be moved relative to the outer shell 14 along longitudinal axis 13.

The probe 16 is designed as an elongated pin 16A extending along the longitudinal axis 13, having a first end 18A facing the connection end 9 and a second end 18B facing the working end 11. A part of the probe 16 can be moved out of the outer shell 14 through an opening 17 (see FIG. 2B) in the outer shell 14 at the working end 11, however in the installed state the first end 18A of the probe 16 facing the connection end 9 is always held in the interior of the hollow outer shell 14 of the drilling tool 5.

The abrasive working end 11 of the drilling tool 5, which also has its own, separate inventive aspect, is described below. Such an abrasive working end 11 can thus also be used with other drills or drilling tools, which in particular have no sensors or sensors other than those described in more detail below for detecting a relative movement between the outer shell and the probe.

At the abrasive working end 11 of the drilling tool 5, a bar 43 is provided for, that is an integral component of the hollow outer shell 14 or is connected with the latter. The bar 43 spans the opening 17 of the outer shell 14 or the substantially cylindrical internal borehole in the outer shell 14 that is connected to the opening 17. Alternatively, the bar 43 extends from one side of the outer shell 14 over the opening 17 or the internal borehole of the outer shell 14 to a second side of the outer shell 14. Preferably, the bar 43 is located in the middle of the outer shell 14, so that the longitudinal axis 13 of the drilling tool 5 emerges through the bar 43 (see in particular FIG. 2A). Preferably, the bar 43 has two lateral walls or lateral surfaces 45A and 45B that are substantially flat or planar. Each lateral surface 45A, 45B ends at its distal end facing away from the connection end 9 in an edge 46A or 46B (see FIG. 1), at which a free end surface 47 of the bar 43 is connected. As can particularly be seen in FIG. 2A, the free end surface 47 is preferably curved or circular arc-shaped in a cross sectional view, and particularly preferably has at its apex a recess 48 with edges.

On the bar 43 one or more abrasive elements, particularly blades, are provided for. In accordance with a preferred embodiment, each of the two edges 46A, 46B is divided into two parts 46A1, 46A2, 46B1 and 46B2, particularly by the recess 48, wherein always only one partial edge 46A1 or 46A2 on the lateral surface 45A and one partial edge 46B1 or 46B2 on the lateral surface 45B is designed as an abrasive blade or cutting edge. Particularly preferably, both partial edges designed as cutting edges (relative to the central axis 13) are diametrically opposite one another, as shown for example in FIG. 1: The partial edge 46A1 on the lateral surface 45A and the partial edge 46B2 on the opposite lateral surface 45B are formed as cutting edges. In particular, those edges of the recess 48 that are connected to the cutting edges 46A1, 46B2 and preferably also at least parts of the lateral edges 44A (see FIG. 1) and 44B (see FIG. 2B) connected to the cutting edges 46A1, 46B2 and laterally delimiting the lateral surfaces 45A, 45B are designed as blades. In accordance with one embodiment, a section of each lateral edge 44A and 44B immediately adjacent to the cutting edges 46A1 and 46B2 is designed as a blade having a length of about 0.5 mm-3.0 mm, preferably about 1.0 mm. The partial edges 46A2 and 46B1 are not designed as cutting edges and are preferably somewhat rounded and/or axially (relative to the longitudinal axis 13) and relative to the cutting edges 46A and 46B2 somewhat recessed.

To form the abrasive lateral edges 44A and 44B, there are two planar recesses 50 on the cylindrical outer sheath 49 of the drilling tool 5 (only one of these can be seen in FIG. 1), which, when the drilling tool 5 is operated, also serve to discharge material shavings, particularly bone shavings, removed by the cutting edges.

The bar 43 is shown in FIGS. 1, 2A and 2B as a straight or "I-shaped" element with two edges 46A and 46B. Of course, the bar can also have other shapes and/or more edges, in order to achieve greater abrasiveness. For example, bar 43 can be implemented with a "Y" shape, and thus have at least three cutting edges (one cutting edge on each of the three arms of the "Y") or bar 43 can be implemented with an "X" shape, and thus have at least four cutting edges (one cutting edge on each of the four arms of the "X"). As shown in FIGS. 1, 2A and 2B, the two cutting edges 46A1 and 46B2 are arranged offset from one another by the width of the bar 43. Alternatively, it is also possible to design the bar in such a way that the two cutting edges 46A1 and 46B2 form a continuous line.

In accordance with the embodiment shown in FIGS. 1, 2A and 2B, the probe 16 is rotated along with the outer shell 14 when the latter is set in motion, for which purpose a rotating carrier mechanism 51 is provided for on the drilling tool 5. In accordance with a preferred embodiment, the lateral surfaces 45A and 45B of the bar 43 are part of the rotating carrier mechanism 51, which pass on the rotational movement generated by the drive 10 and transmitted via the connection end 9 to the hollow outer shell 14 to the probe 16 held in the outer shell 14. At its second end 18B, the probe 16 has a probe tip 36, which is arranged eccentrically to the longitudinal axis 13. At the probe tip 36 there is at least one substantially flat or planar contact surface 36A, which is in contact with one of the two lateral surfaces 45A and 45B of the substantially centrally located bar 43. Through this contact between the surfaces 36A and 45A or 45B, the rotational movement is transferred from the outer shell 14 to the probe 16. Of course, other types of rotating carrier mechanism 51 can also be implemented, for example in the form of a polygon, particularly a hexagon, wherein a section of the probe 16 has a polygonal outer form and a corresponding section of the inner wall of the hollow outer shell 14 likewise has a polygonal form.

In accordance with the embodiment shown in FIGS. 1, 2A, and 2B, the probe 16 has no abrasive element for removing material, and thus does not separate any material from the item to be handled, particularly tissue. The probe tip 36 is accordingly rounded off. Of course, it would, however, also be possible in accordance with another embodiment, to equip the probe with an abrasive element for removing material, in particular with a cutting tip on the distal end facing the material 55.

To be able to place the probe 16 and any additional components in the interior of the hollow outer shell 14 of the drilling tool 5, the outer shell 14 is constructed in two parts, wherein the two parts 14A and 14B can be (particularly detachably) connected to one another using suitable connection mechanisms. The connection mechanisms can be designed, for example, as screw, plug-in or bayonet connections. The two outer shell components 14A and 14B can be manufactured from different materials or the same material, for example can be made of metal, particularly steel, and/or plastic, wherein in particular the outer shell component 14B having the abrasive end 11 is preferably made of metal, and possibly the outer shell part 14A surrounding the electromagnetic sensor 19 to be described below is at least partially made of plastic, so as not to interfere the function of the sensor 19, or to interfere it less. In particular when the electromagnetic sensor 19 is implemented as an inductive sensor 21, it is advantageous for at least that part of the outer shell 14 provided for in the vicinity of the inductive sensor 21 to be manufactured from a non-magnetic material, for example aluminum, non-magnetic steel, plastic or ceramic, for example a ceramic material including zirconium.

FIGS. 2A and 2B show a device 1 for quickly stopping a medical, particularly dental, drilling tool, in particular of the drilling tool 5 shown in FIG. 1. In addition to the drilling tool 5, the device 1 also includes an electromagnetic sensor 19, that is designed to detect a relative movement between the outer shell 14 and the probe 16. The sensor 19 is placed along or within the longitudinal extension L of the body 12 of the drilling tool 5. The sensor 19 thus does not project beyond the two ends 9 and 11 of the drilling tool, or projects only insignificantly. It can furthermore be seen that a part of the sensor 19 is located in the drilling tool 5 and another part of the sensor 19 outside the drilling tool 5.

As shown in FIGS. 2A and 2B, the electromagnetic sensor 19 is designed as a contact-free inductive sensor 21, comprising at least one coil 22, located outside the drilling tool 5, but near its outer shell 49, and a coil core 23. Said at least one coil 22 may, for example, surround the drilling tool 5 in an annular form. The coil core 23 comprises a magnetic element that can be moved relative to the coil 22. The magnetic element is either a separate element with a fixed connection to the probe 16 so that it can be moved together with the probe 16 or the magnetic element is formed by the probe 16, for example by the probe 16 being manufactured from a magnetic material or having been magnetized during manufacture, as shown in FIGS. 2A and 2B. The coil core 23 is in particular formed by the first end 18A of the probe 16, which is held in the interior of the hollow outer shell 14.

The probe 16 and/or the coil core 23 are pre-tensioned by a spring element 15 in the direction of the abrasive end 11 of the drilling tool 5, so that at least a part of the probe 16 or of the probe tip 36 projects out through the opening 17 or projects beyond the hollow outer shell 14, in particular the bar 43. The spring element 15 is shown in FIGS. 2A, 2B as a hose section made of an elastic material, particularly an elastic plastic, but it can, of course, also include other springs, in particular spiral or leaf springs, for example also made of metal.

The detection of a relative movement between the outer shell 14 and the probe 16 by the inductive sensor 21 proceeds as follows: If a force impinges upon the probe 16 that counteracts the spring load of the spring element 15, and that is great enough to compress the spring element 15, then the probe 16 and/or the coil core 23 and/or the magnetic element move axially along the longitudinal axis 13 towards the connection end 9 of the drilling tool 5. The coil core 23 thus enters or penetrates into or further into the coil 22. Coil 22 is connected to an alternating current source and is supplied with AC power from it. As the coil core 23 or the magnetic element penetrate (further) into the coil 22, their inductance thus changes, so that a relative movement between the outer shell 14 of the drilling tool 5 and the coil core 23 or the probe 16 can be deduced. The change in inductance is transmitted in the form of a sensor signal to a control and/or regulatory device 39 connected with the sensor 19 (see FIG. 6), which, based on this sensor signal, stops the drive 10 for the drilling tool 5.

A relative movement between the outer shell 14 and the probe 16 in particular occurs when the drilling tool 5 reaches a transitional area between two materials with different hardnesses, in particular in the medical field a transitional area from a hard tissue, such as bone, to a soft tissue, such as a membrane, muscular or connective tissue, cerebral matter, or even to a hollow space (possibly filled with a fluid or a gas). Corresponding embodiments, also for dental use, in particular for drilling through the bone of the upper jaw during a sinus floor elevation, are described in the patent application DE 10 2008 032 704 A1 cited above, which is incorporated herein by reference.

The first end 18A of the probe 16 is preferably radially (relative to the longitudinal axis 13) broadened, or designed as a flange or flange-like broadening, in order to thus create a stable and sufficiently large contact surface for the spring element 15 and/or an improved functioning of the sensor 19, by the parts of the sensor 19 located within and outside the drilling tool 5 being positioned as closely as possible together in space. At least the radially broadened end 18A, preferably also the spring element 15, are incorporated into a likewise radially broadened section of the body 12 or the outer shell 14 of the drilling tool 5.

The drilling tool 5 has a channel 20 for a treatment fluid and/or cooling fluid extending along the longitudinal axis 13. The channel 20 starts at an opening 52 on the outermost end of the connection end 9. This opening 52 permits the channel 20 to be connected to a fluid source that, for example, provides a physiological saline solution or an anesthetic or a fluid for lifting a membrane. The connection to the fluid source is, for example, provided via a small tube that can be inserted through the opening 52 into the channel 20, and which, possibly via another tube, is connected to the fluid source. If necessary, there are one or more sealing elements, for example O-rings, provided for on the small tube or on the drilling tool 5, for example at the opening 52 or in the channel 20, which prevent the fluid from seeping out of the small tube or the channel 20.

The channel 20 runs along the longitudinal axis 13 in the interior of the outer shell 14 and is formed in the section adjacent to the opening 52 by the internal borehole 31 of the hollow outer shell 14. Thereafter, the channel 20 passes through the spring element 15 or continues within it or passes by it. In the embodiment shown in FIGS. 2A, 2B, the spring element 15 has a borehole 53, so that the fluid can flow through the spring element 15 and then further into a borehole 32 in the probe 16. The borehole 32 likewise extends axially through the probe 16 along the longitudinal axis 13, opening out into a cross hole 35 at its end facing the probe tip 36. The cross hole 35 penetrates the probe 16 radially to the longitudinal axis 13 and has at least one opening 54, which opens out into a gap 34, in particular an annular gap, formed by an offset of the outer wall of the probe 16 from the inner wall of the hollow outer shell 14. The gap 35 finally ends in the opening 17, through which the fluid emerges from the drilling tool 5, in particular from the outer shell 14. Alternatively or additionally, it is possible for the borehole 32 to lead to the second end 18B of the probe 16, so that at least a part of the fluid is dispensed via an opening in the probe 16.

To be able to form the gap 34, the probe 16 has two sections arranged axially one after the other: A guide section 33A, whose diameter corresponds roughly to the inner width of the hollow outer shell 14, so that the guide section 33A is supported on the inner wall of the hollow outer shell 14, and a second section 33B whose diameter is less than the inner width of the hollow outer shell 14, so that the probe 16 in this section 33B is offset from the interior wall of the outer shell 14, producing the gap 34. The guide section 33A supports the probe 16 on the interior wall of the hollow outer shell 14 and to guide or slide the probe 16 within the outer shell 14.

FIGS. 3A-3C, 4, and 5 show additional devices 2, 3 and 4 for quickly stopping a medical or dental drilling tool 6, 7, 8. Both the devices 2, 3 and 4 and the drilling tools 6, 7 and 8 resemble the quick stop device 1 and the drilling tool 5 described above in their structure and function, so that identical components bear the same reference numbers. Therefore preferably the differing features of the quick stop devices 2, 3 and 4 will be described below.

Figure 3A:
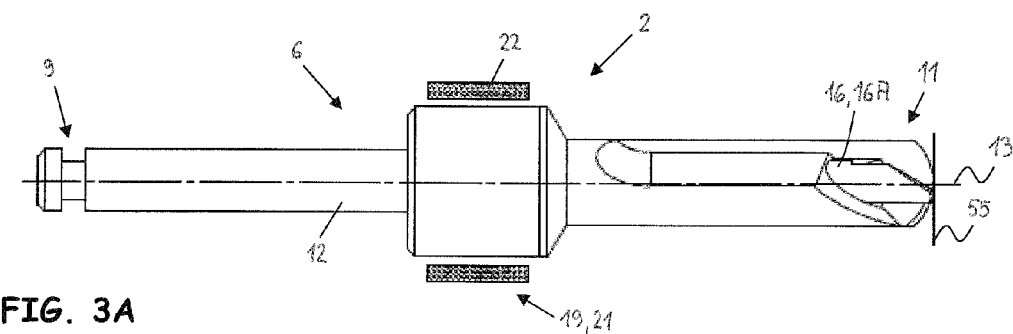
FIG. 3A shows an exterior view of another embodiment of a quick stop device wherein the drilling tool is placed on a surface so that the probe tip of the probe is inserted into the outer shell of the drilling tool against the force of the spring element.
Figure 3B:
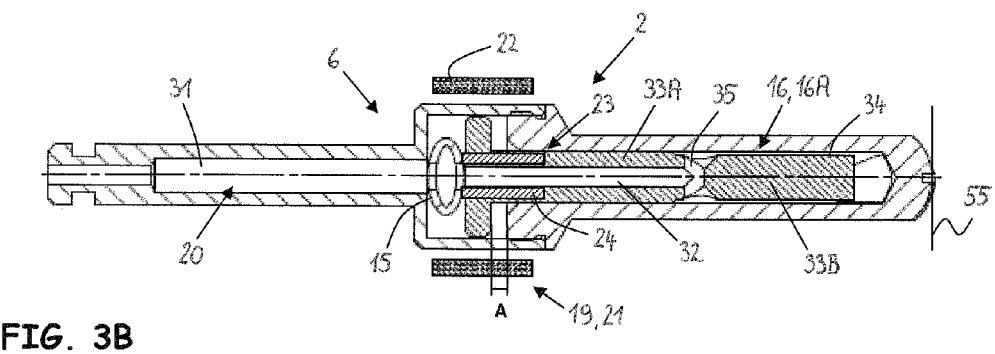
FIG. 3B shows a cross-section through the quick stop device in FIG. 3A, illustrating a first sectional plane.
Figure 3C:
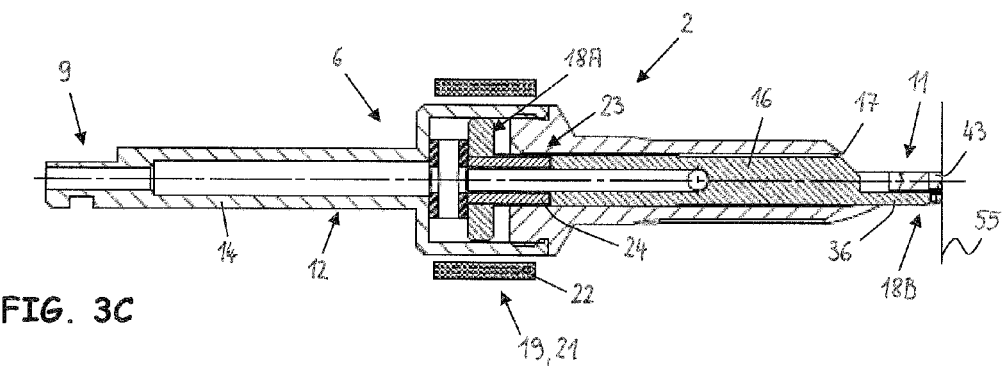
FIG. 3C shows another cross-section through the quick stop device in FIG. 3A, illustrating a second sectional plane that is rotated through an angle of 90° relative to the first sectional plane.

The quick stop device 2 shown in FIGS. 3A-3C comprises an electromagnetic sensor 19 for detecting a relative movement between the outer shell 14 and the probe 16. The sensor 19 is, in turn, designed as an inductive sensor 21, wherein the coil core 23 comprises a magnetically soft ferrite body 24, which, in the case of a relative movement between the probe 16 and the hollow outer shell 14 and/or between the coil 22 and the coil core 23, changes the inductance of said at least one coil 22. The ferrite body 24 is connected to the probe 16 in such a way that it moves together with the probe 16. The ferrite body 24 is preferably incorporated into a recess in the probe 16. The ferrite body 24 is preferably designed as a cylinder or hollow cylinder, that is arranged concentrically on the probe 16. Particularly preferably, the channel 20 runs through the hollow cylindrical ferrite body 24. Of course, the ferrite body can also have different shapes, for example be attached as a ferrite rod onto the probe 16.

In FIGS. 3A-3C it can also be seen that the drilling tool 6 is placed onto a hard material 55, for example a bone tissue. This situation occurs, for example, when the user places the drilling tool 6 onto material 55 before starting to drill, or during drilling into the material 55. The probe 16, and thus the coil core 23, are forced against the spring load of the spring element 15 into the hollow outer shell 14 (towards the connection end 9), so that the free end of the probe tip 36 is largely flush with bar 43 (see in particular FIG. 3C). The spring element 15 is accordingly compressed. If the drilling tool 6 is removed from the material 55 or if the drilling tool 6 penetrates the material 55, or if the drilling tool 6 is about to break through the material 55, then the spring element 15 is slackened and moves the probe 16 and the coil core 23 in the direction of the abrasive end 11, so that at least a part of the probe tip 36 projects out of the hollow outer shell 14, particularly beyond the bar 43 (as shown in FIGS. 2A and 2B). The sliding of the probe 16 relative to the outer shell 14 brings about the change in inductance of the coil 22 and leads to the drive of the drilling tool 5, 6 immediately being stopped, as already described above. In order to obtain a clear and easily evaluated sensor signal, the displacement A (see FIG. 3B) of the probe 16 or the coil core 23 should be at least 0.2 mm, preferably at least 0.3 mm.

In accordance with one embodiment, the diameter of the coil 22 of the inductive sensor 21 amounts to about 5-8 mm, the winding count of the coil 22 to about 20-40, the length of the ferrite body 24 to about 2-3 mm, and the effective voltage applied to about 0.7-1.0 V.

Figure 4:
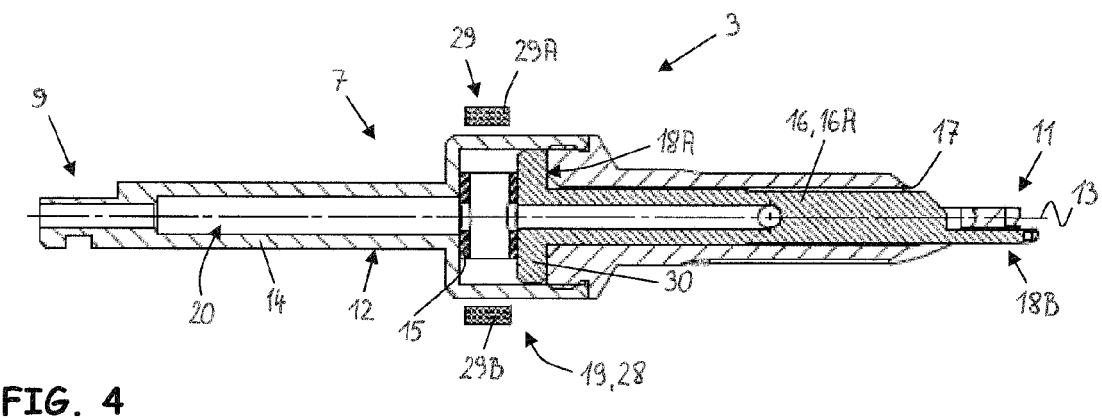
FIG. 4 shows a cross-section through an embodiment of a quick stop device having a capacitive sensor.

The quick stop device 3 for a medical, particularly dental, drilling tool 7 shown in FIG. 4 has a contact-free electromagnetic sensor 19 for detecting a relative movement between the outer shell 14 and the probe 16, which is designed as a capacitative sensor 28. The capacitative sensor 28 comprises at least two metallic electrodes 29, 30, which form a capacitor, wherein one electrode 30 can be moved relative to another electrode 29 by means of the relative movement of the probe 16 to the outer shell 14. The electrodes 29, 30 are connected to an alternating current power source via electric lines, and form a high-frequency oscillating circuit, in which an electrical field is generated. The relative movement of the two electrodes 29, 30 causes a change in capacitance, and thus a change in the amplification in the oscillator circuit. The change in capacitance and/or change in amplification is passed on in the form of a sensor signal to a control and/or regulatory device 39 connected to the sensor 28 (see FIG. 6), and, based on the sensor signal, said control and/or regulatory device stops the drive 10 for the drilling tool 7.

Preferably, one electrode 30 of the capacitor is connected to the probe 16 or formed by the probe 16, in particular by a metallic section of the probe 16. The electrode 30 is thus incorporated into the drilling tool 7. Particularly preferably, the electrode 30 is provided for on the radially broadened end 18A of the probe 16, or is formed by this end 18A. Another electrode 29 is arranged outside the drilling tool 7 along or within the longitudinal extension of the body 12 of the drilling tool 7. The capacitative sensor 28 thus does not project beyond the two ends 9, 11 of the drilling tool 7, or not significantly.

In accordance with a particularly preferred embodiment, the capacitative sensor 28 comprises at least two substantially plate-shaped electrodes 29A and 29B, as well as a measurement electrode 30 that can be moved with the probe 16 along the longitudinal axis 13 of the drilling tool 7 and relative to the two substantially plate-shaped electrodes 29A and 29B. The plate-shaped electrodes 29A and 29B are located outside the drilling tool 7 along or within the longitudinal extension of the body 12 of the drilling tool 7. The two plate-shaped electrodes 29A and 29B are particularly designed as a bridge circuit.

Figure 5:
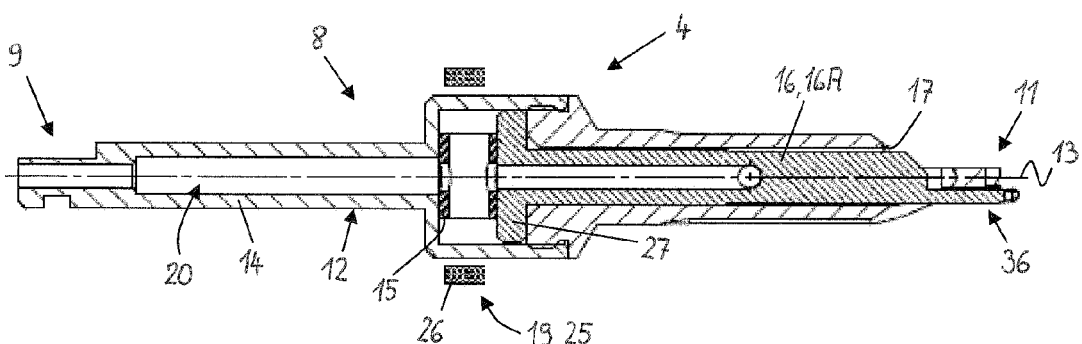
FIG. 5 shows a cross-section through an embodiment of a quick stop device having a magnetic sensor.

The device 4 for quickly stopping a medical or dental drilling tool 8 shown in FIG. 5 has an electromagnetic sensor 19 for detecting a relative movement between the outer shell 14 and the probe 16, which is designed as a magnetic sensor 25. The probe 16 has a magnetic element 27 which, as described for FIGS. 2A and 2B, either has a fixed connection to the probe 16 in order to be moved together with the probe 16, or is formed by the probe 16, for example by the probe 16 being manufactured from a magnetic material or having been magnetized during manufacture, as shown in FIG. 5. The magnetic element 27 is thus, in turn, held in the interior of the hollow outer shell 14.

Outside the drilling tool 8, however along or within the longitudinal extension of the body 12 of the drilling tool 7, at least one magnetic sensor 26 is arranged, for example a Hall effect sensor or a reed sensor, which detects a magnetic parameter of the magnetic element 27, for example the magnetic field strength. The relative movement between the outer shell 14 and the probe 16 brings about a change in the distance between the magnetic element 27 and the magnetic sensor 26, and thus a change in the value of the magnetic parameter at the magnetic sensor 26. For example, the magnetic field strength of the magnetic field generated by the magnetic element 27 falls off at the magnetic sensor 26 when the probe 16 having the magnetic element 27 slides in the direction of the abrasive end 11 during or after the penetration of the drilled material. The change in the value of the magnetic parameter is, in turn, passed on in the form of a sensor signal to a control and/or regulatory device 39 connected to the sensor 25 (see FIG. 6), and, based on this sensor signal, said control and/or regulatory device 39 stops the drive 10 for the drilling tool 8.

To assist the functioning of the sensor 25, preferably that part of the hollow outer shell 14 at which the sensor 25 is located is made of a non-metallic material, for example plastic.

Figure 6:
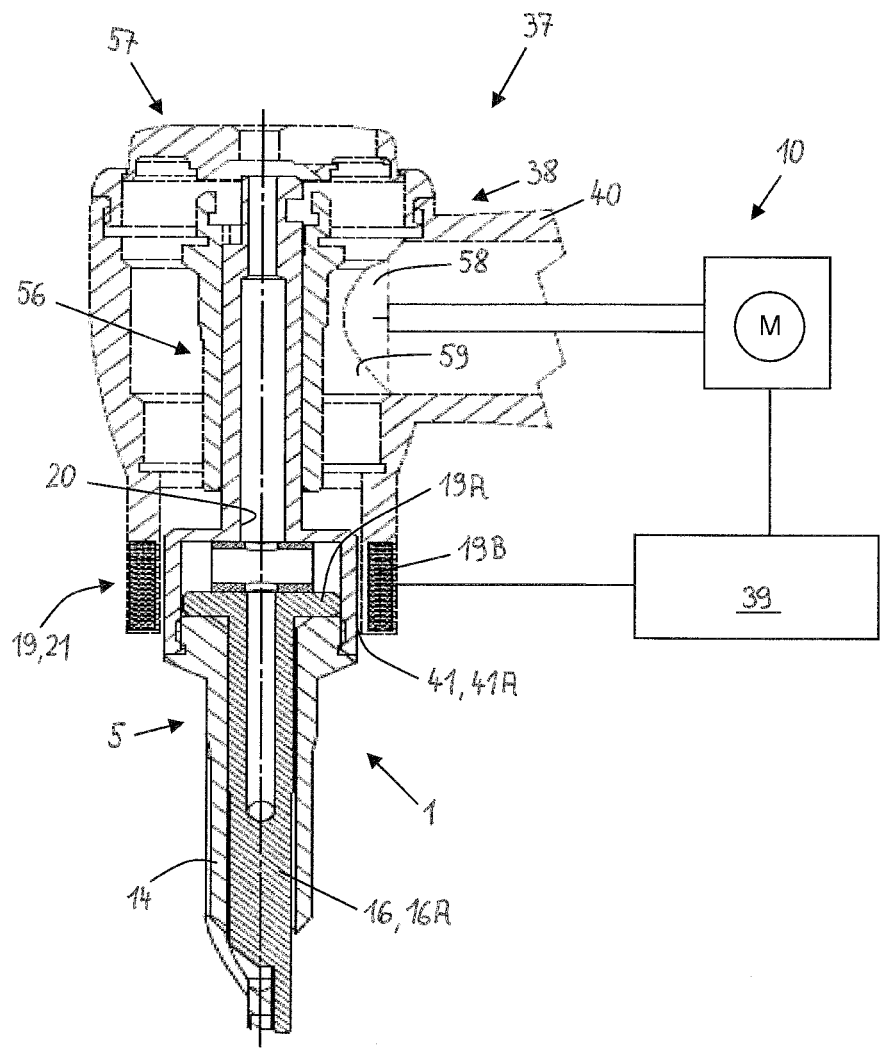
FIG. 6 shows a partly schematic view of an embodiment of a medical or dental treatment device having a device for quickly stopping a drilling tool, a drive for the drilling tool, a handpiece to connect the drilling tool and a control and/or regulatory device for receiving a sensor signal generated by the electromagnetic sensor and for stopping the drive.

FIG. 6 shows a medical or dental treatment device 37, which, for example, comprises the device 1 for quickly stopping a medical or dental drilling tool 5. Of course, the treatment device 37 can also have the other quick stop devices 2, 3, 4 and the corresponding drilling tools 6, 7 and 8 described above, so that the following description of FIG. 6 is purely an example and also correspondingly applies to the other quick stop devices 2, 3 and 4 and the other drilling tools 6, 7 and 8.

The treatment device 37 furthermore comprises a drive 10 for the drilling tool 5, a handpiece 38 for connecting the drilling tool 5, and a control and/or regulatory device 39 for receiving a sensor signal generated by the electromagnetic sensor 19 and stopping the drive 10. The treatment device 37 can preferably have devices for processing the sensor signal from the sensor 19, for example to streamline, filter or amplify the signal, wherein such devices are particularly provided for in the control and/or regulatory device 39, or are formed as part of the control and/or regulatory device 39.

The handpiece 38 is preferably designed as a contra-angle handpiece with a laterally located tool insertion opening 41. The handpiece 39 has a hollow outer or gripping shell 40, in whose head section a tool connection device or chuck 56 is provided for that can be set into a working movement. The tool connection device 56 can particularly be made to rotate and is preferably mounted on roller bearings. Through a release device 57, the drilling tool 5 can be released from the tool connection device 56 again. In particular, the tool connection device 56 is designed as a positive tool connection device, for example as a holder for a 2.35 mm standard drill.

The tool connection device 56 is operatively connected with the drive 10, so that the drive 10 sets the tool connection device 56 and the drilling tool 5 into a working motion, particularly into rotation. The drive 10 comprises, for example, a controllable motor, in particular an electric motor, one or more shafts, a gear, couplings, and/or gearwheels. The direct transmission of the drive movement from the drive 10 to the tool connection device 56 is carried out via a gearwheel 58 provided for on the drive and a pinion gear 59 attached to the tool connection device 56 that engages with the gearwheel 58.

The control and/or regulatory device 39 is connected to the drive 10, particularly the motor, and to the sensor 19, through electrical wires and/or signal wires. In that regard, the line for the sensor 19 can run within the handpiece 38, particularly within the outer shell 40, and/or outside the handpiece 38.

The control and/or regulatory device 39 has a power source or is connected to a power source and supplies the sensor 19 with electrical power, especially with the alternating current required. The control and/or regulatory device 39 controls and/or regulates the operation of the motor of the drive 10, in particular it supplies the motor with power or determines the rotational speed and/or torque, and stops the motor when the electromagnetic sensor 19 detects a relative movement between the outer shell 14 and the probe 16. Preferably, the control and/or regulatory device 39 comprises a microcontroller or microcomputer. On the control and/or regulatory device 39 there can, furthermore, be control elements for the user to select or set operating parameters of the treatment device 37 and/or a display for displaying operating parameters.

Since, during the drilling process, little relative movement can occur between the outer shell 14 and the probe 16, which would already generate a sensor signal without the drilling tool already having penetrated or being near to penetrating the material 55, there is preferably a threshold value laid down in the control and/or regulatory device 39, or a threshold can be set by the user, which the sensor signal of the sensor 19 needs to exceed for the control and/or regulatory device 39 to stop the drive 10.

In accordance with one embodiment, the sensor 19 is located in the area of the tool insertion opening 41 of the handpiece 38.

In accordance with the embodiment shown in FIG. 6, at least a part 19B of the electromagnetic sensor 19, 21, is located in on or the handpiece 38, particular directly, and preferably attached directly to or in the outer shell 40 of the handpiece 38. The component 19B of the sensor 19 thus forms an integral component of the handpiece 38 that has a fixed connection to the handpiece 38. In contrast, the other component 19A of the sensor 19 has a fixed connection to the drilling tool 5 and forms an integral component of the drilling tool 5. If the drilling tool 5 is connected to the handpiece 38, then the two components 19A, 19B of the sensor 19 are arranged in such a way that they are operatively connected to one another, in order to detect a relative movement between the outer shell 14 and the probe 16.

In accordance with a preferred embodiment, the tool insertion opening 41 has a section or area where the component 19B of the sensor 19 that is integral to the handpiece 38 is located, for example the coil 22 of the inductive sensor 21 or an electrode 29 (plates 29A and 29B) of the capacitative sensor 28. Particularly preferably, the tool insertion opening 41 has a broadened section 41A, where the component 19B of the sensor 19 that is integral to the handpiece 38 is located, and that is used to hold the other component 19A of the sensor 19. In particular, the broadened section 41A is dimensioned in such a way that the component 19A of the sensor 19 or the first end 18A of the probe 16 can be held in it. Alternatively, the handpiece 38, particularly the outer shell 40, has at least one extension in the area of the tool insertion opening 41, where the component 19B of the sensor 19 that is integral to the handpiece 38 is located.

Figure 7A:
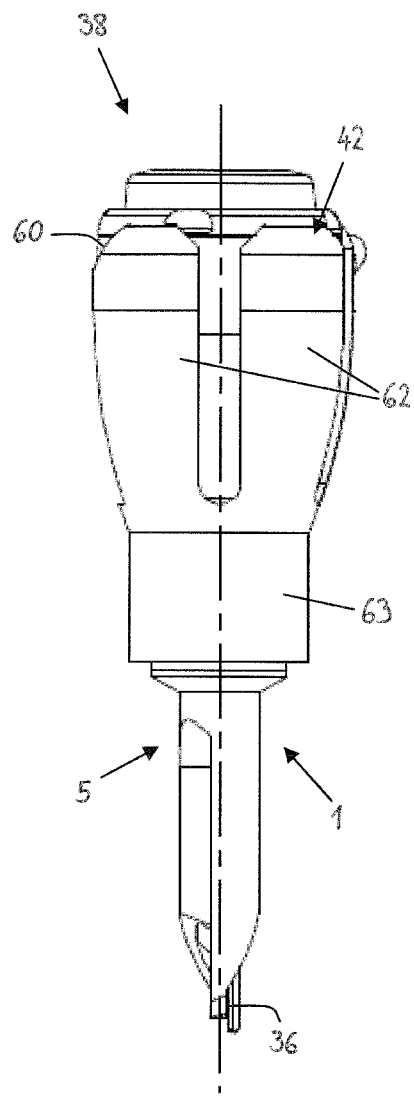
FIG. 7A is an elevation view showing a medical, particularly dental, treatment device having a device for the quick stop of a medical, particularly dental, drilling tool that is detachably connected to a handpiece.
Figure 7B:
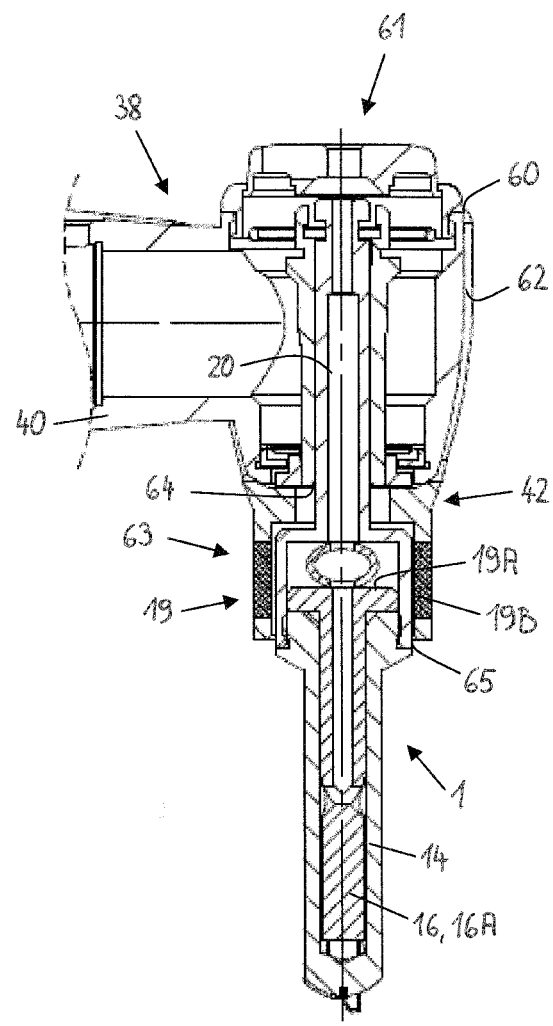
FIG. 7B is a sectioned elevation view of the device shown in FIG. 7A, but rotated through an angle of 90° relative to FIG. 7A.

FIGS. 7A and 7B show an alternative embodiment of a medical or dental treatment device, in which the entire sensor 19 is detachably connected to the handpiece 38. The sensor 19 is again shown using the example of an inductive sensor 21 with the drilling tool 5, but, of course, the treatment device can also have the other quick stop devices 2, 3, 4 and the corresponding drilling tools 6, 7, 8 described above, so that the description of FIGS. 7A and 7B below is again merely an example and applies accordingly to the other quick stop devices 2, 3, 4 and the other drilling tools 6, 7, 8. Furthermore, FIGS. 7A and 7B only show the handpiece 38 and the quick stop device 1, but this treatment device also has a drive, a control and/or regulatory device and corresponding electrical connections between the components, just as described for FIG. 6.

The sensor 19, in turn, has two components 19A and 19B, that, when they are attached to the handpiece 38, are operatively connected with one another so as to detect a relative movement between the outer shell 14 and the probe 16. The component 19A of the sensor 19 has a fixed connection to the drilling tool 5 and forms an integral component of the drilling tool 5. Through the connection of the drilling tool 5 to the handpiece 38, the component 19A can be detachably connected to the handpiece 38. The second component 19B of the sensor 19 can be attached directly to the handpiece 38 using a detachable connecting device 42, in particular to the outer shell 40 of the handpiece 38. The detachable connecting device 42 can, for example, be designed as a screw, plug-in or clamping connection. Accordingly, the first component 19A and the second component 19B of the sensor 19 are located on the outside of the outer shell 40 or outside the outer shell 40 of the handpiece 38.

In accordance with the preferred embodiment shown in FIGS. 7A and 7B, the detachable connecting device 42 is implemented as a plug-in connection that has a support 60 for inserting or incorporating the head section 61 of the handpiece 38. The support 60 comprises, for example, two or more spring arms 62 for fastening to the head section 61 and a detection section 63 connected to the spring arms 62 having the component 19B of the sensor 19. The spring arms 62 are in particular pre-tensioned inwards in the direction of the support 60, so that the diameter of the support 60 is somewhat less than the diameter of the head section 61. If the head section 61 is inserted into the support 60, then the spring arms 62 are moved somewhat outwards radially and clamp the head section 61. If the head section 61 is removed from the support 60, then the spring arms 62 move back radially inwards to their starting position.

The detection section 63 is preferably formed as an annular, sleeve-like or hollow cylindrical element in or on which the component 19B of the sensor 19 is provided, in particular the coil 22 of the inductive sensor 21 or an electrode 29 (plates 29A and 29B) of the capacitative sensor 28. The detachable connecting device 42 is preferably designed in such a way that the detection section 63, particularly the component 19B of the sensor 19, can be arranged at the tool insertion opening 64 of the handpiece 38 or connect directly to it or be flush with it. The inner width of the borehole 65 of the detection section 63 is dimensioned in such a way that the drilling tool 5 can be held in it, in particular the component 19A of the sensor 19 provided for on the drilling tool 5 or the first end 18A of the probe 16.

In a preferred method for drilling a material 55, a device 1, 2, 3, 4 described above for quickly stopping a medical or dental drilling tool 5, 6, 7, 8 or a medical or dental treatment device 37 is used, wherein the drive of the drilling tool 5, 6, 7, 8 is stopped when the electromagnetic sensor 19 detects a relative movement between the outer shell 14 and the probe 16 of the drilling tool 5, 6, 7, 8, particularly a relative movement exceeding a threshold value. The material 55 is preferably a human or animal tissue, preferably a bone tissue, particularly a jawbone.

A preferred use of the device 1, 2, 3, 4 for quickly stopping a medical or dental drilling tool 5, 6, 7, 8 described above or a medical or dental treatment device 37 as described above is carried out when drilling through a human or animal upper jawbone, particularly during a sinus floor elevation.

The scope of protection is not limited to the embodiments described here but instead comprises all embodiments deploying or including the basic, analogous functional principle. In addition, all the features of all the embodiments described and illustrated here may be combined with one another.

What is claimed is:

1. A device for quickly stopping a medical or dental drilling tool comprising:
   a drilling tool with a connection end for connecting to a drive, an abrasive working end for removing material and a body extending between the connection end and the working end having a longitudinal extension extending along a longitudinal axis of the drilling tool, wherein the drilling tool has a hollow outer shell in which a probe pre-tensioned by a spring element is held, wherein the probe is movable along the longitudinal axis relative to the outer shell such that at least a part of the probe is movable out of the outer shell through an opening in the outer shell at the working end, wherein the probe is designed as an elongated pin extending along the longitudinal axis having a first end facing the connection end and a second end facing the working end, and
   an electromagnetic sensor for detecting a relative movement between the outer shell and the probe, wherein
   the first end of the probe facing the connection end is held in the interior of the hollow outer shell of the drilling tool, wherein
   the electromagnetic sensor is arranged along the longitudinal extension of the body of the drilling tool, and wherein
   the drilling tool has a channel for a treatment fluid extending along the longitudinal axis.

2. A device according to claim 1, wherein the electromagnetic sensor comprises an inductive sensor with at least one coil and a coil core, wherein said at least one coil and coil core can be moved relative to one another through the movement of the probe relative to the outer shell.

3. A device according to claim 2, wherein the coil core can be moved with the probe along the longitudinal axis of the drilling tool and relative to the at least one coil.

4. A device according to claim 1, wherein the electromagnetic sensor comprises a magnetic sensor and at least one magnetic element, wherein the magnetic sensor and said at least one magnetic element can be moved relative to one another through the movement of the probe relative to the outer shell.

5. A device according to claim 1, wherein the electromagnetic sensor comprises a capacitive sensor having at least two metallic electrodes, which form a capacitor, wherein one electrode can be moved relative to another electrode through the movement of the probe relative to the outer shell.

6. A device according to claim 5, wherein the capacitive sensor comprises at least two substantially plate-shaped electrodes and a measurement electrode that can be moved with the probe along the longitudinal axis of the drilling tool and relative to the two substantially plate-shaped electrodes.

7. A device according to claim 1, wherein the channel for a treatment fluid comprises at least one of a borehole in the outer shell of the drilling tool and a borehole in the probe of the drilling tool.

8. A device according to claim 1, wherein the channel for a treatment fluid passes through a spring element which pre-tensions the probe.

9. A device according to claim 1, wherein the probe comprises a guide section, whose diameter corresponds approximately to the inner width of the hollow outer shell, so that the guide section is supported on the inner wall of the hollow outer shell, and the probe comprises a second section that is separated from the inner wall of the hollow outer shell by a gap, wherein the gap forms at least a part of the channel for a treatment fluid.

10. A device according to claim 9, wherein a borehole in the probe which forms at least a part of the channel for a treatment fluid and the gap are connected with one another through a cross hole in the probe.

11. A device according to claim 1, wherein the probe comprises at its second end facing the working end a probe tip arranged eccentrically to the longitudinal axis.

12. A treatment device comprising
a device for quickly stopping a medical or dental drilling tool according to claim 1,
a drive for the drilling tool,
a handpiece for connecting to the drilling tool and
a control and/or regulatory device for receiving a sensor signal generated by the electromagnetic sensor and stopping the drive, wherein at least a part of the electromagnetic sensor is arranged on or in the handpiece.

13. A treatment device according to claim 12, wherein the sensor is positioned in the area of a tool insertion opening of the handpiece.

14. A treatment device according to claim 12, wherein
a first part of the sensor is provided for on the drilling tool and is detachably connectable to the handpiece by connecting the drilling tool to the handpiece, and
a second part of the sensor is attachable directly to the handpiece through a detachable connection device, so that when the first part and the second part of the sensor are attached to the handpiece, the first part and the second part of the sensor are operatively connected with one another.

15. A treatment device according to claim 14, wherein at least one of the first part of the sensor and the second part of the sensor is arranged on the outside of the outer shell or outside the outer shell of the handpiece.

16. A method for using a medical or dental drilling tool that comprises a device for quickly stopping the drilling tool, a connection end for connecting to a drive, an abrasive working end for removing material, and a body extending between the connection end and the working end having a longitudinal extension extending along a longitudinal axis of the drilling tool, wherein the drilling tool has a hollow outer shell within which a first end of a probe pre-tensioned by a spring element is held, the probe being movable along the longitudinal axis relative to the outer shell such that at least a part of the probe is movable out of the outer shell through an opening in the outer shell at the working end, wherein the probe is designed as an elongated pin extending along the longitudinal axis with a second end facing the working end, and an electromagnetic sensor is positioned on the longitudinal extension for detecting a relative movement between the outer shell and the probe, the drilling tool having a channel for a treatment fluid extending along the longitudinal axis, the method comprising:
stopping the drive of the drilling tool when the electromagnetic sensor detects a relative movement between the outer shell and the probe of the drilling tool.

17. A method for using a medical or dental drilling tool according to claim 16, comprising drilling at least one of a human or animal tissue, a human or animal bone tissue, or a human or animal jawbone.

18. A device according to claim 1, wherein the drilling tool is configured for drilling through a human or animal upper jawbone during a sinus floor elevation.

19. A method for using a medical or dental drilling tool that comprises a device for quickly stopping the drilling tool, a drive for the drilling tool, and a handpiece for connecting to the drilling tool, the device having a connection end for connecting to the drive, an abrasive working end for removing material, and a body extending between the connection end and the working end having a longitudinal extension extending along a longitudinal axis of the drilling tool, wherein the drilling tool has a hollow outer shell within which a first end of a probe pre-tensioned by a spring element is held, the probe being movable along the longitudinal axis relative to the outer shell such that at least a part of the probe is movable out of the outer shell through an opening in the outer shell at the working end, wherein the probe is designed as an elongated pin extending along the longitudinal axis with a second end facing the working end, and an electromagnetic sensor is positioned on the longitudinal extension for detecting a relative movement between the outer shell and the probe, further comprising a control and/or regulatory device for receiving a sensor signal generated by the electromagnetic sensor, the method comprising:
stopping the drive of the drilling tool when the control and/or regulatory device receives signals indicating that the electromagnetic sensor detects a relative movement between the outer shell and the probe of the drilling tool.

20. A method for using a medical or dental drilling tool according to claim 19, wherein the method comprises performing a sinus floor elevation.

* * * * *